United States Patent [19]

Kulish et al.

[11] Patent Number: 4,718,699
[45] Date of Patent: Jan. 12, 1988

[54] GAS SYSTEM OUTLET STATION ASSEMBLY

[75] Inventors: Stanley J. Kulish, Chesterfield; Bidwell C. Cranage, Ferguson, both of Mo.; James F. Mariol, Cincinnati; Robert P. Swank, Mansfield, both of Ohio

[73] Assignee: Allied Healthcare Products, Inc., St. Louis, Mo.

[21] Appl. No.: 466,280

[22] Filed: Feb. 14, 1983

[51] Int. Cl.$^4$ ............................................. F16L 25/00
[52] U.S. Cl. ........................................ 285/12; 285/24; 285/93
[58] Field of Search ..................... 285/12, 24, 25, 26, 285/27, 28, 29, DIG. 15, 93; 137/551, 360, 329.1

[56] References Cited

U.S. PATENT DOCUMENTS

| | | | |
|---|---|---|---|
| 2,908,511 | 10/1959 | Rogers | 284/1 |
| 3,287,031 | 11/1966 | Simmons et al. | 285/27 |
| 3,448,760 | 6/1969 | Cranage | 137/360 |
| 3,544,257 | 12/1970 | Cranage | 137/360 |
| 3,563,267 | 2/1971 | Thompson | 137/329.1 |
| 3,643,985 | 2/1972 | Cranage | 285/189 |
| 3,774,636 | 11/1973 | Arita | 285/24 |
| 4,123,089 | 10/1978 | Viero et al. | 285/39 |

Primary Examiner—Dave W. Arola
Attorney, Agent, or Firm—Dickstein, Shapiro & Morin

[57] ABSTRACT

A gas service outlet station is disclosed having a gas-unique keying system which permits the provision of specific keying for a large number of gas services with the use of relatively few universal parts. In preferred forms, the outlet station face plate assemblies are removable from the corresponding valve bodies without destroying the required gas-unique keying between the face plate assembly, valve body and gas service box.

11 Claims, 11 Drawing Figures

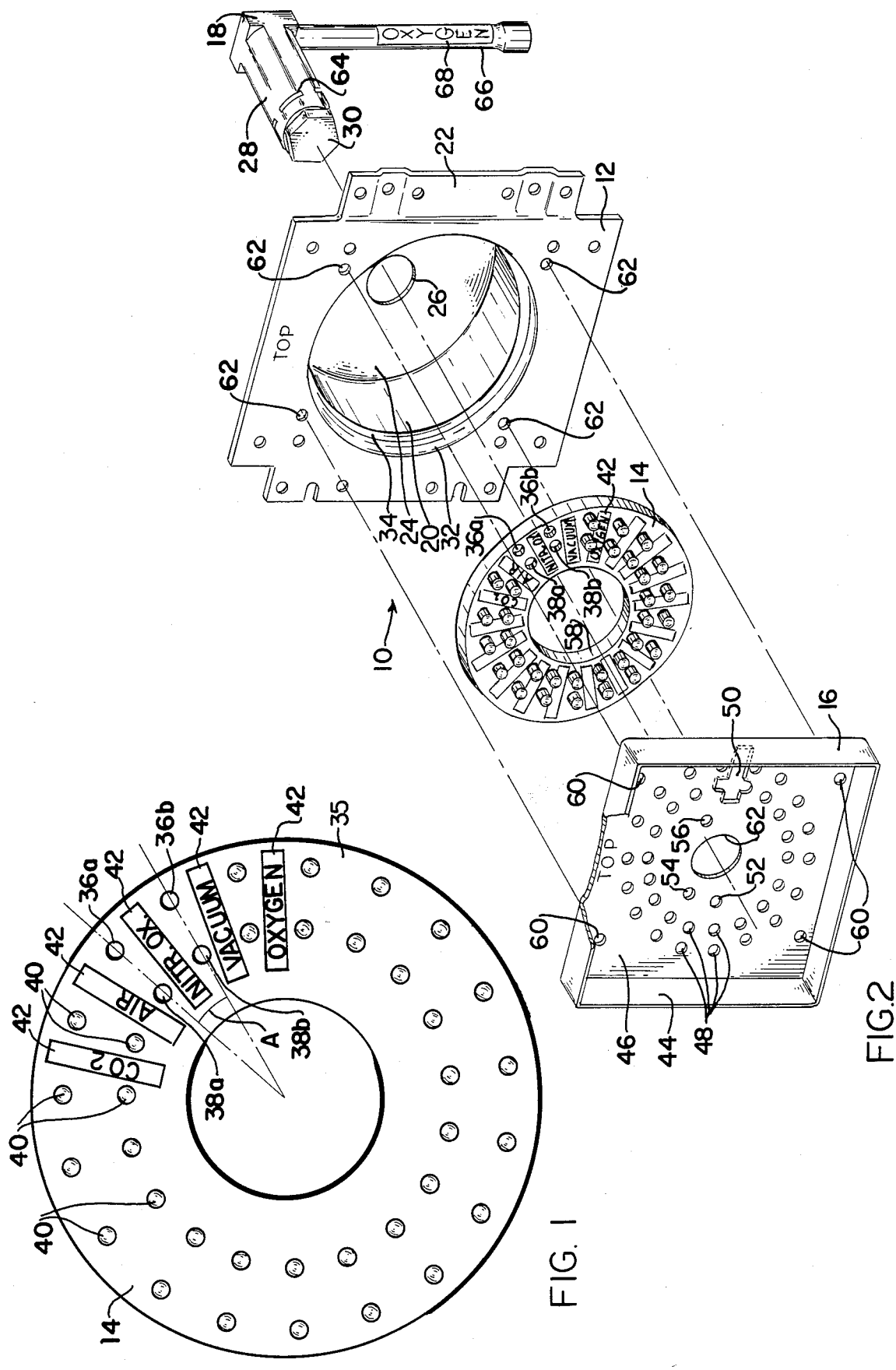

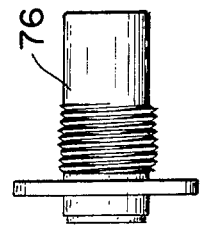
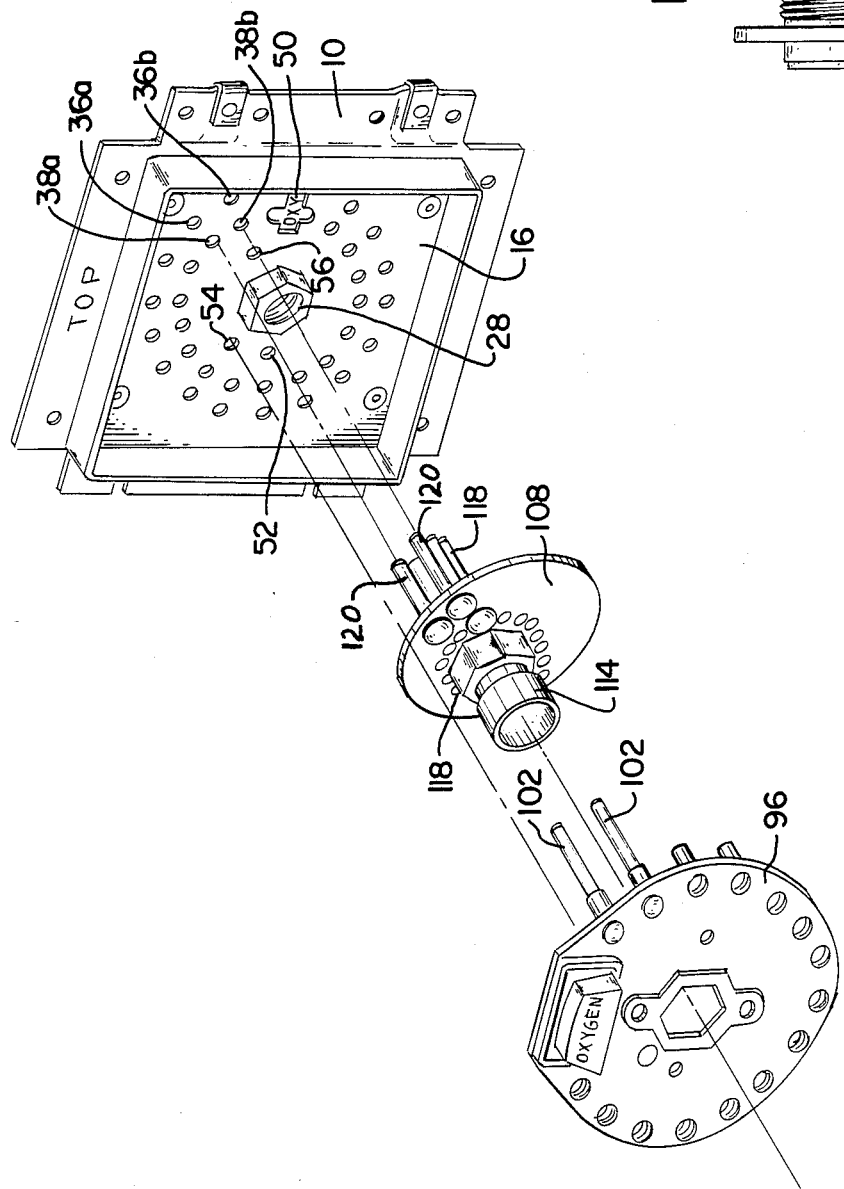

GAS SYSTEM OUTLET STATION ASSEMBLY

BACKGROUND OF THE INVENTION

Pressurized gas supply networks are known in which it is required to provide a gas outlet station which cooperates with a detachable adaptor for selective transfer of gas flow under pressure from a gas supply conduit via such adaptors to secondary equipment for ultimate use of the gas.

For example, in medical treatment environments, it is commonplace to have available in a plurality of treatment areas wall or ceiling mounted gas outlet stations which are supplied by a permanently installed gas supply system with such medically useful gases as nitrogen, carbon dioxide, air, oxygen or nitrous oxide, each usually being supplied from a storage tank which may be quite remote from any area of ultimate use of the gas. Such outlet stations may also include a vacuum or suction line connection or other desirable gaseous fluid flow service connections.

For each different gas or service available at an outlet station the outlet station commonly includes an adaptor connection assembly which is opened when connected with the proper adaptor to deliver gas via the adaptor to the connected secondary equipment or user, and is closed leak tight when the adaptor is disconnected therefrom to preclude leakage of pressurized gas from the system into the ambient air.

Each adaptor connection assembly in the outlet station typically may be mounted together with a face plate assembly and a mounting box which is permanently installed in the wall or ceiling of the treatment area and to which the proper gas supply conduit is routed.

In the prior art of such gas supply systems it is known to provide schemes of non-redundant keying to ensure error free gas connections. For example, such keying schemes have been applied to ensure proper adaptor-to-outlet station connections. Two common approaches to such adaptor keying are the DISS or Diameter Indexed Safety System, and the Quick Connect System. In DISS, the gas outlet valves for each of a plurality of different gases or services include specified diametrical dimensioning for adaptor receiving portions thereof which differ from the corresponding dimensions of all other such outlet valves whereby only one of a corresponding plurality of adaptors will fit each such outlet valve. In the Quick Connect or QC System each adaptor includes an elongated valve plug which is engagable with the respective outlet valve when manually thrusted into engagement therewith. The engagement establishes a leak tight gas flow connection and the connection is secured or latched by a pin latch mechanism separate from the valve plug. The latching pin and the elongated valve plug commonly are disposed in spaced parallel relationship with the spacing therebetween defining a keyed relationship such that each quick connect adaptor is engagable only with an outlet station having a corresponding lateral spacing between the valve element and the latch pin engaging mechanism.

Just as proper adaptor-to-outlet station connections are of critical importance in medical gas supply systems, so too are proper matching of the various outlet station valves, face plates and latching assemblies to the permanently installed mounting box and the gas supply conduit associated therewith. The potential severity of the consequences of improper outlet station assembly is of such magnitude as to dictate a very high standard of care. Accordingly, non-redundant keying schemes are also known in the art for keying outlet valves to mounting boxes, face plate assemblies to valves or mounting boxes, and the like, in order to ensure error free assembly of the various outlet station components during system installation.

The prior art includes numerous examples of gas outlet station valve assemblies and cooperating adaptors, of which the following are exemplary: U.S. Pat. Nos. 2,908,511, 3,448,760, 3,544,257, 3,563,267, and 3,643,985.

Notwithstanding the efficacy of prior keyed assembly schemes, certain shortcomings of the prior art have been noted. For example, the commercial acceptance of two connection systems, QC and DISS, has precipitated the evolution of two distinct and mutually incompatible approaches to outlet station construction thus severely limiting the use of universal components in gas supply system design. Another shortcoming of some prior art designs has been the failure thereof to provide for non-redundant keying in all installation configurations. For example, in some wall mounted systems designers have relied on the obvious up and down orientation of the face plate or other components to establish proper orientation thereof (e.g., the component is properly oriented when a label or other indicia thereon is upright). This approach functions more in the nature of a guide than a keying scheme and as such does not necessarily offer the desired non-redundancy of a proper keying scheme. In ceiling outlet station installations of such systems the up and down orientation guide is lost thus introducing the possibility of improper assembly.

Still another shortcoming reflected in the prior art has been the need in DISS systems for a keying system which non-redundantly keys all components without requiring the DISS valve body to be carried on the face plate assembly. In this regard, it has been found advantageous to permit the DISS face plate assembly to be removed from the outlet station without removing the DISS valve whereby to allow ready access to the in-place valve for the purpose of performing leak check inspection during routine maintenance. However, Key Systems for DISS outlet stations have heretofore either provided no keying for the DISS valve, or have required the permanent attachment of the valve to the DISS face plate.

Additionally, prior art keying systems for both DISS and QC services have required an inventory of many gas-specific parts by manufacturers of the keyed outlet stations. This shortcoming has encouraged such manufacturers to limit the number of gas-specific selections for users of outlet stations because the production of low quantities of stations for unusual gas services has heretofore proved uneconomical.

SUMMARY OF THE INVENTION

Inasmuch as gas service system installation is beyond the supervisory reach of the system component manufacturers, it is highly desirable that the system components include suitable design features to ensure their proper installation. Accordingly, the present invention contemplates an improved gas system outlet station which resolves the above and other shortcomings of the prior art. According to a presently preferred embodiment of the instant invention, there is provided a universal mounting box which includes an indexable means coordinated with an indicia display whereby, when the indicia display indicates a given gas service, a non-redundant keying scheme is established in the box which will permit installation therewith of only those valve, face plate, latch and other requisite components corresponding to the indicated gas service. The box and indicia element are factory assembled in a predetermined keying configuration with a correspondingly labeled gas supply conduit connector, and are supplied as an integral unit. Thus, a completely non-redundant gas outlet station assembly is provided which precludes improper component installation with the mounting box.

A further aspect of the present invention includes the capability of the universal mounting box to accept for assembly therewith components of either the QC or the DISS type corresponding to the gas service indicated. Independent keying for DISS valves is also provided.

An additional feature of the present invention is the provision of a keying system whereby gas-specific components for a large number of different gas services can be manufactured from universal parts. The invention thus provides for improved assurance of proper outlet station installation and enhanced prospects for universal parts applicability, including the attendant manufacturing and installation cost benefits.

FIG. 1 is a frontal elevation of an indexable indicia element for use in conjunction with the instant invention;

FIG. 2 is an exploded perspective showing the manner of assembly of the indicia element of FIG. 1 within a mounting box;

FIG. 10 is an exploded perspective showing assembly of the DISS face plate assembly (with face plate and insert removed for clarity) and the DISS valve carrier element of FIGS. 8 and 9 into the mounting box.

FIG. 11 is a side elevational view of a QC primary valve body.

Figure 4:
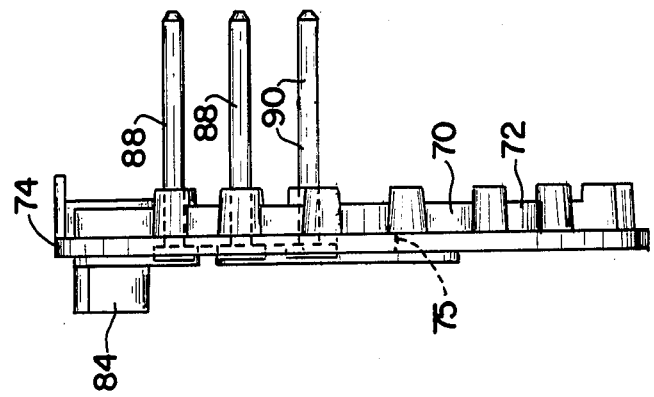
FIG. 4 is a side elevation taken on line 4—4 of FIG. 3.

To proceed with a description of one presently preferred embodiment of the invention, there is generally indicated at 10 in FIG. 2 a gas outlet station mounting box assembly including a box portion 12, an indexable indicia portion 14, a box cover portion 16 and a gas supply connection assembly 18.

Box portion 12 includes a generally stepped cylinder 20 and a formed flanged portion 22 located adjacent an open end of cylinder 20. The opposite axial end of cylinder 20 is completely closed by a lateral wall portion 24 but for an aperture 26 formed in wall 24 coaxially with the cylinder 20. Aperture 26 receives a valve engaging end portion 28 of connector assembly 18, shown in FIG. 2 with a test plug 30 in place.

Cylinder 20 includes adjacent the flange portion 22 an enlarged diameter portion 32 which is dimensioned to receive indicia element 14 therein and is of such axial length that in the assembled box indicia element 14 is captively retained between box cover 16 and a forwardly facing shoulder 34. Referring to FIG. 1, indicia element 14 will be seen to include a generally disc-like body 35 of molded plastic or the like having indexable key receiving means shown as pairs of through openings 36 a, 36 b and 38 a, 38 b, each such pair of openings being located preferably at circumferentially spaced locations on respective larger and smaller diameter pitch circles which are coaxial with body 35. Throughout the remaining circumferential extent of the pitch circles upon which openings 36 a, 36 b and 38 a, 38 b reside, there are provided respective pluralities of studs 40, each being spaced from the adjacent studs 40 or from the openings 36 a, 36 b and 38 a, 38 b if adjacent thereto, by an angle of magnitude A. Radially oriented labels 42, corresponding to a plurality of gas services for which the box assembly 10 might be used, are positioned circumferentially intermediate selected circumferentially adjacent pairs of studs 40 and/or openings 36 a, 36 b and 38 a, 38 b.

Box cover 16 includes a flange portion 44 encompassing a lateral wall portion 46. Wall portion 46 includes a plurality of through openings 48 arranged in a pattern to register with studs 40 and openings 36 a, b and 38 a, b in a plurality of coaxial orientations of indicia element 14 with respect to box cover 16. For each of such registered orientations one of the labels 42 will register with a window 50 formed in box cover 16 to indicate which of the several gas services is to be available from that particular box.

Both the box portion 12 and box cover 16 are marked to distinguish top from bottom as a guide for factory assembly of the mounting box 10 and to indicate proper orientation for wall mounting. In such factory assembly, indicia element 14 is located coaxially adjacent the backside of box cover 16 with the desired label 42 displayed through window 50 and with studs 40 engaged within corresponding openings 48 of box cover 16. The resultant location of openings 36 a, b and 38 a, b defines a non-redundant keying scheme to ensure on-site installation of the gas-specific DISS valve bodies and face plate assembly and the gas-specific QC face plate assembly corresponding to the gas service displayed in window 50. Also provided by box cover 16 are orientation openings 52, 54 and 56, all of which reside within the diameter of an enlarged central opening 58 in indicia element body 35 and are therefore unaffected by the orientation of body 35 with respect to box cover 16. Orientation openings 52, 54 and 56 contribute to a non-redundant keying scheme which ensures proper orientation of the outlet station elements with respect to box 10 as will be described.

Indicia element 14 is secured with respect to box cover 16 in the desired orientation by permanent mounting of cover 16 upon flange 22 of box 12 whereby indicia element 14 is captively retained within cylinder portion 32 between lateral wall 46 of cover 16 and shoulder 34. Cover 16 is permanently affixed to box 12 as by rivets (not shown) or the like permanently disposed within cooperably registered corner openings 60, 62 in cover 16 and box flanged 22, respectively.

It will be appreciated that the marking of cover 16 and box 12 to indicate the top of each is merely a guide for proper factory assembly and for upright installation.

This guide has no bearing on the non-redundant keying scheme being described herein as the keying scheme is established by virtue of the orientation of indicia element 14 with respect to box cover 16.

The gas connector assembly 18 has valve engaging end portion 28 thereof inserted from the backside of box assembly 10 through opening 26 and opening 58, and through a coaxial opening 62 in lateral wall 46. A suitable securing element such as a snap ring (not shown) is engaged within a groove 64 formed adjacent the free end of valve engaging portion 28 so as to reside forwardly of or adjacent to the outer side of lateral wall thus securing gas connector assembly 18 within the box assembly 10.

To provide guidance in proper connection of the gas supply to box assembly 10 at the construction site, a pigtail portion 66 of gas connection assembly 18 includes a label 68 corresponding to the gas service indicia displayed in window 50.

The above described box assembly provides for a non-redundant keying scheme to assure that only the proper outlet station components, whether of the QC or the DISS type, may be assembled with the box 10. Furthermore, the box 10 as assembled in the factory will accept either OC or the DISS type components for the indicated gas service.

The factory assembly of box 10 of course does not ensure that the proper gas supply will be connected at the construction site to pigtail 66; however, the accuracy of such connections are certified by independent verification. In any event, when the proper gas supply is connected, the subsequent installation of the proper QC or DISS components for that gas supply or service is ensured.

Figure 3:
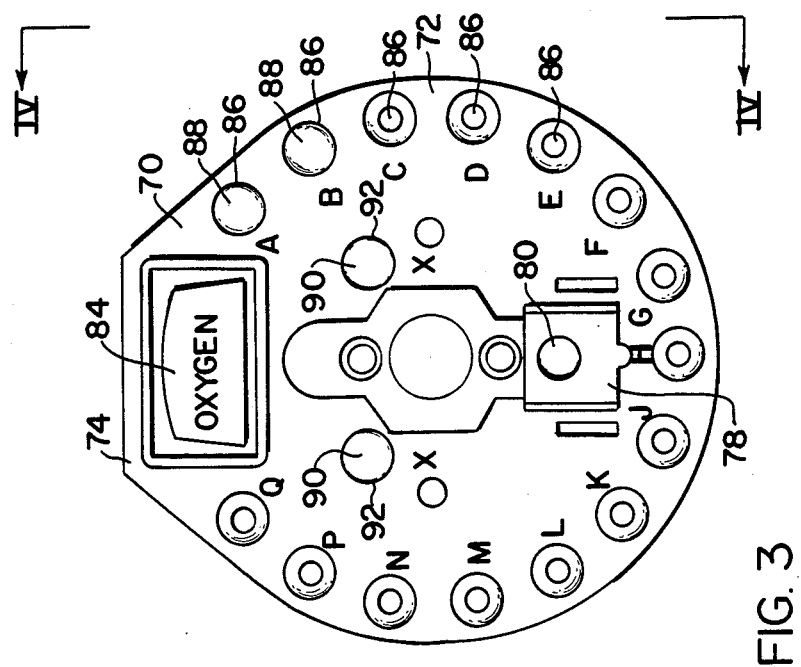
FIG. 3 is a frontal elevation of a QC index plate.
Figure 5:
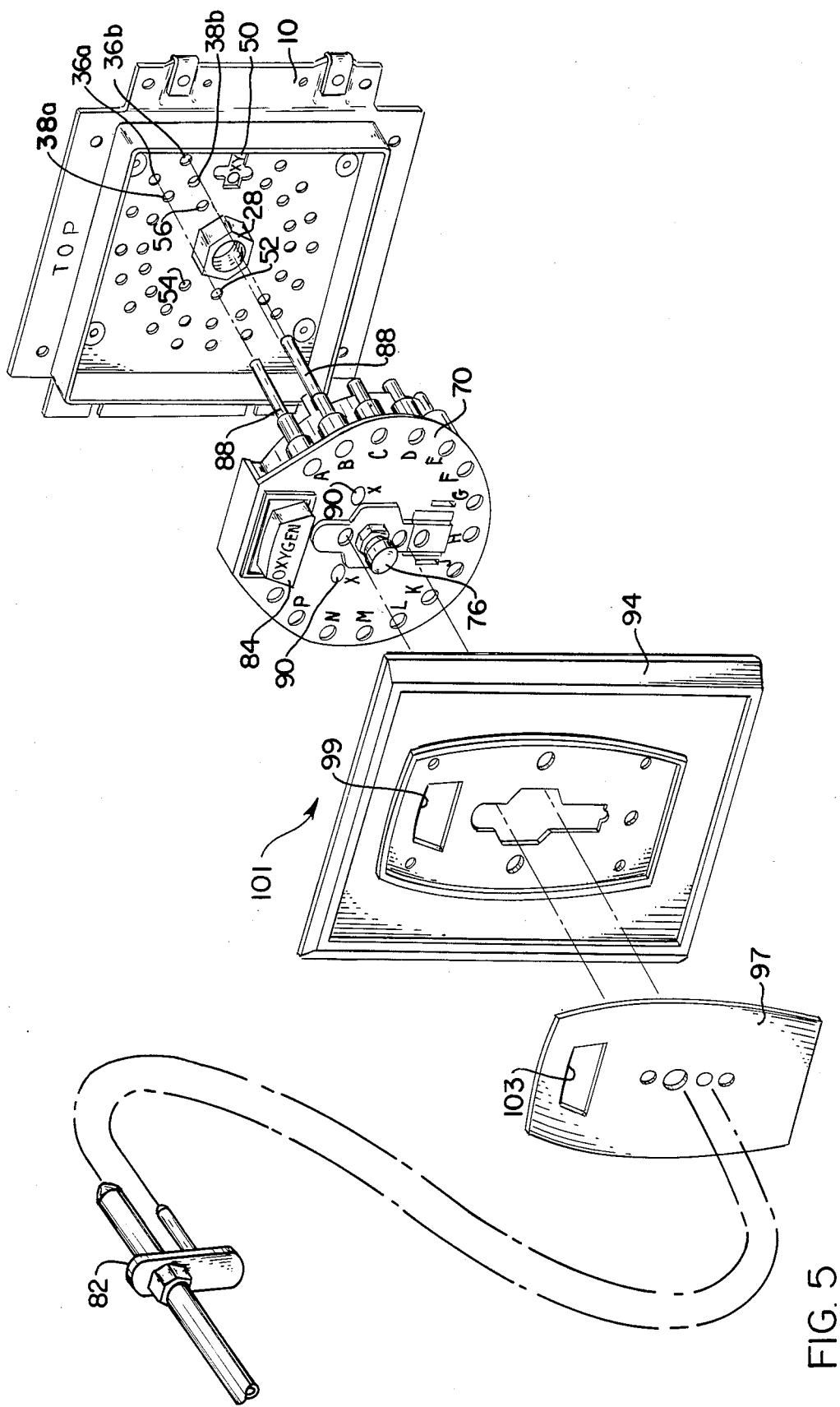
FIG. 5 is an exploded perspective showing the assembly of the QC face plate assembly into the mounting box and of a facia or cover plate and a cover plate insert.
Figure 7:
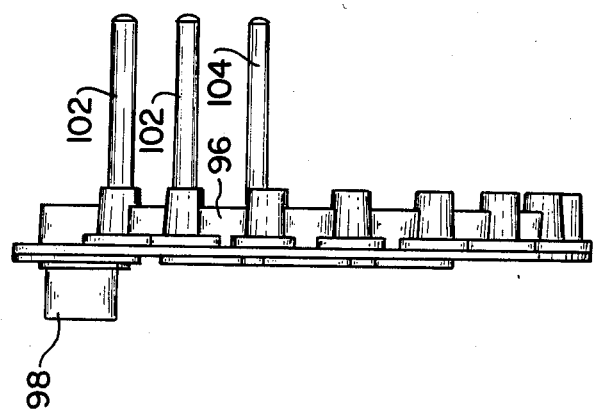
FIG. 7 is a side elevation taken on line 7—7 of FIG. 6.

Referring now to FIGS. 3, 4 and 5, there is shown at 70 in FIGS. 3 and 4 a QC index plate assembly for use in conjunction with a box assembly 10. Index plate 70 includes a rigid body member 72 of molded plastic for example, formed as a generally disc-like structure and including an upwardly projecting top portion 74. A central opening 75 is sized to accommodate a QC valve body 76. The valve body 76 (as shown in FIG. 11) is adapted to be threadably received within the engaging portion 28.

Index plate 70 also includes a conventional factory assembled spring latch (not shown) adapted to releasably retain an adapter striker pin 81 which forms a part of the QC adaptor 82 (FIG. 5). A key insert 78 on the front side of plate 70 has a striker pin receiving aperture 80 whose geometry and spacing from the mounted valve 76 is uniquely cooperable with the QC adaptor 82 for an oxygen service connection. Also included in factory assembly of index plate 70 is the provision of a gas-specific push-to-release button 84 which operates the spring latch above-described.

To provide for correct assembly of the described QC oxygen service face plate and latch assembly, body member 72 is provided with a series of through openings 86 which are located for coaxial registry with certain of the openings 48 on the larger diameter pitch circle of box cover 16. Individual openings 86 may be indentified by any suitable indicia such as A, B, C and so forth as shown in FIG. 3 to provide for ready identification thereof during factory assembly. As the illustrated index plate 70 is factory assembled for oxygen service, a non-redundant keying scheme is provided to ensure that it may be assembled only to an oxygen service mounting box 10. For this purpose, keying pins 88 are factory installed in the openings 86 corresponding to oxygen service, which are openings A and B as shown in FIG. 3. Pins 88 will register through the corresponding openings in box cover 16 and through openings 36 a, 36 b in indicia element 14 to non-redundantly key the oxygen service QC face plate assembly into the oxygen service mounting box 10 as will be described.

It will be appreciated that pin 88 in hole 86B can be disposed in hole 86C, 86D, etc. to create multiple unique keys using the same components of index plate 70. Likewise pin 88 in hole 86A can be relocated to establish additional unique keys; in the embodiment shown in FIG. 3, 103 unique keys are available using same components of plate 70. However, for mating with the embodiment of box 10 shown in FIG. 2, it is necessary to maintain angle A relation between the pins 88, consequently this embodiment is limited to fourteen assembly keying possibilities (BC, CD, DC, etc.) In order to increase the number of assembly keying combinations it is necessary to modify indicia plate 14 to redefine angle A.

An additional keying feature is provided by other pins 90 factory installed in orientation openings 92 formed in index plate 70 and identified thereon by the letter X. Openings 92 are so located that pins 90 installed therein will register with orientation openings 54 and 56 in box cover 16 to provide non-redundant orientation of the QC face plate assembly (described below) with respect to box 10.

As shown in FIG. 5, index plate 70 mates with a conventional facia plate 94 and a mating gas-unique insert 97. Plate 94 and insert 97 are riveted or otherwise permanently attached to index plate 70 at the factory to thereby form a face plate assembly 101 uniquely keyed to mate with box 10 if and only if index plate 70, insert 97 and box 10 are all unique to the same gas service. When insert 97, plate 94 and assembly 70 are interfitted, button 84 projects through complemental openings 97, 103, respectively in plate 94 and insert 97 to provide user access to the identifier-latch button 84, and the abutting relationship of plate 94 against index plate 70 serves to hold the pins 88, 90 captively in place.

In field assembly of face plate assembly 101 with box 10 (FIG. 5) the installer first compares the latch button identifier 84 with the indicia display in window 50 to assure that he is attempting to install the proper face plate assembly into the proper box. He then aligns the face plate assembly 101 in its proper orientation such that pins 88 register with openings 36 a, 36 b and pins 90 register with openings 54 and 56. The oxygen face plate assembly, when properly oriented by registry of pins 90 with openings 54 and 56, will assemble only with an oxygen service box because the openings 36 a, 36 b in any box for another gas service will occupy a different position and will not accept pins 88.

Figure 6:
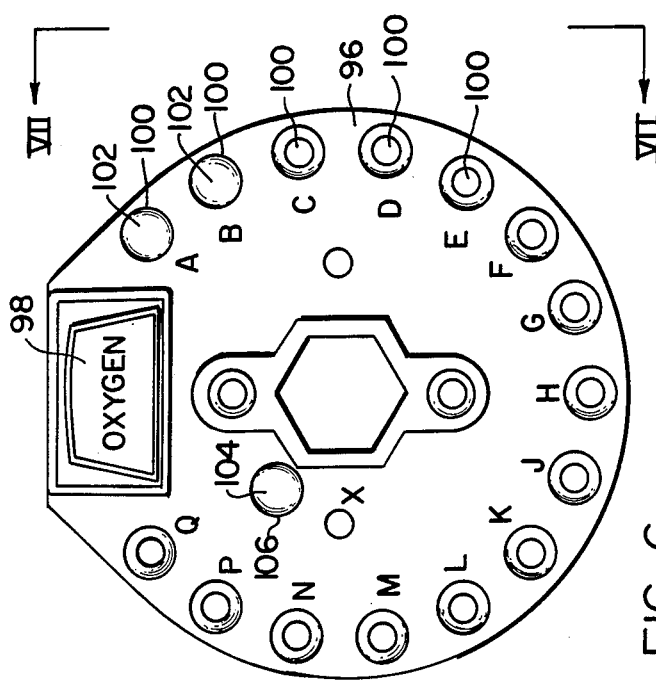
FIG. 6 is a frontal elevation of a DISS face plate assembly.

Referring now to FIGS. 6 through 10, there is indicated in FIG. 6 an index plate 96 for a DISS type gas service outlet station and similar to the above described QC index plate but for the following differences. DISS index plate 96 does not provide any latching function as DISS valves typically have adaptor latching or securing capability. Accordingly, the permanently installed oxygen indentifier button 98 on index plate 96 is a service identifier only without any latch disengagement function. Index plate 96 includes pin receiving openings 100 labeled A through Q and located identically to openings 86 of the QC index plate 70. For oxygen service, pins 102 are factory installed in the openings 100 labeled A and B, just as in the QC index plate 70, to register with openings 36 a, 36 b in oxygen service mounting box 10.

Index plate 96 is also provided with an orientation pin 104 factory installed in an orientation opening 106 which is labeled X on the index plate 96. Orientation pin 104 registers with opening 54 of box 10 when index place 96 is properly oriented with respect thereto for assembly.

Figure 9:
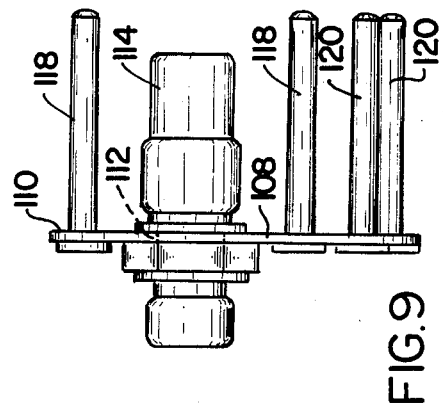
FIG. 9 is a top plan view taken on line 9—9 of FIG. 8.
Figure 8:
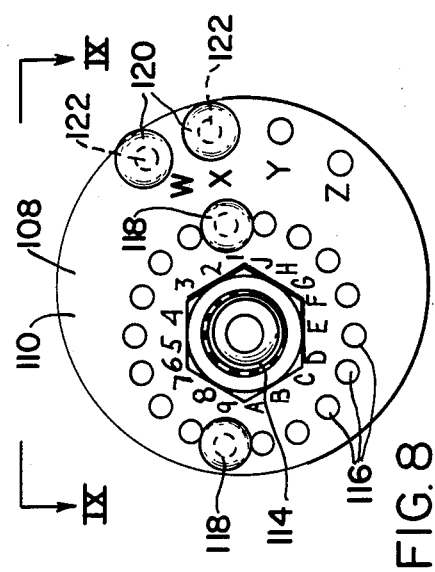
FIG. 8 is a frontal elevation of a DISS valve carrier element.

Although factory assembly of the proper DISS valve to each DISS index plate may be feasible, it is preferred to provide the DISS valve with its own keying element as shown in FIGS. 8 and 9 for installation with box 10. As with the QC system, the DISS index plate 96 is permanently attached to a facia plate and plate insert similar in all material respects to plate 94 and insert 95 to form a DISS face plate assembly (not shown).

In FIGS. 8 and 9 a DISS valve assembly 108 includes a rigid plate member 110, generally disc-like as shown, and having an eccentrically-positioned through opening 112 within which a DISS oxygen service valve 114 is non-removably installed at the factory. The plate 110 is a universal DISS valve keying element having a plurality of pin receiving openings 116 positioned on a pitch circle which is coaxial with the opening 112. Orientation pins 118 are permanently factory installed within two of the openings 116 to provide for keyed installation of valve assembly 108 into box 10. The locations of pins 118 determines the positioning of a pair of gas service keying pins 120 which are factory installed permanently within pin receiving openings 122 formed in plate 110. The angular relationship between the pins 120 can be varied to increase the keying possibilities in a manner similar to the increased keying possibilities for the index plate 70 described above.

The above described DISS outlet station elements are keyed for non-redundant installation with box 10 as shown in FIG. 10. Box 10 is assembled, as before, for oxygen service whereby openings 36 a, 36 b and 38 a, 38 b are located identically as for the above described QC outlet station assembly, and the "oxygen" label is displayed through window 50 of box 10. The DISS oxygen valve assembly 108 is positioned with orientation pins 118 aligned with openings 52 and 56 in box cover 16. In this orientation gas service keying pins 120 are aligned with openings 38 a, 38 b and may be interfitted therewithin upon assembly whereby only an oxygen service DISS valve 114 may be installed in box 10 and connected to connector portion 28. Any other DISS valve will have a uniquely different factory determined pattern of orientation keying pins 118 and gas service identifier keying pins 120 and would not fit the factory determined orientation and service identifier openings set up in the box 10.

After installation of DISS valve assembly 108, DISS face plate assembly, including DISS index plate 96, is installed on box 110 by aligning orientation pin 104 with opening 54 and gas service keying pins 102 with openings 36 a, 36 b. It is noted that all of the orientation pins of all embodiments hereinabove are located on a pitch circle having a common diameter and center (when installed) with the pitch circle upon which orientation openings 52, 54 and 56 are located. Accordingly, in assembling index plate 96 into box 10, pin 104 will pass through the one of orientation pin receiving openings 116 in plate 110 which registers with opening 54 in box cover 16.

According to the description hereinabove there is provided by the instant invention an improved gas outlet station assembly which provides for non-redundantly keyed assembly of the proper gas valve, face plate, latch and other requisite components into a universal gas service mounting box assembly. The universal mounting box is provided with indexable indicia display and key receiving means to provide for factory assembly, using the same component parts, of boxes for any of a wide variety of gas service needs. The outlet station elements are provided with corresponding keying elements which may be factory installed to cooperate with any given box configuration to ensure correct on-site installation of the proper outlet station elements with the proper mounting box. Furthermore, the factory assembled box will accept the properly keyed outlet station elements of the DISS or the QC type and conceivably may accept other known or heretofore unknown types of outlet station valving and adaptor latching or other components without alteration of the mounting box assembly. On-site outlet station installation is thus greatly improved and the chance of installation error markedly reduced.

The keying scheme of the present invention carries the keying afforded by the DISS and the QC type adaptor technology back through the outlet station to the mounting box thus assuring that the proper gas service will reach the connected secondary equipment. This key scheme is also inparted independently to the DISS valve for DISS systems.

A presently preferred embodiment of the invention having thus been described, it will be appreciated that the invention is capable of numerous alternative and/or modified embodiments without departing from the broad spirit and scope thereof. Accordingly, it is intended that the invention be construed as broadly as permitted by the scope of the claims appended hereto.

I claim:

1. A face plate assembly for a gas-unique keyed gas delivery system, said assembly comprising:
   an index plate including a universal body member having a front side and a back side and a plurality of apertures each extending therethrough,
   said plate further including indexing pins each adapted to be received within any preselected one of said apertures and having a head on one end thereof configured relative to said apertures to preclude passage of the pin therethrough,
   each said pin being disposed within a preselected one of said apertures and extending outwardly from the back side of said member with said head thereof abutting against said front side whereby said pins collectively define a gas-unique key;
   a gas-unique facia plate adapted to mate with said index plate; and
   means for mounting said facia plate on said front side of said index plate in abutment against said pin heads to captively retain said pins within said preselected apertures.

2. A face plate assembly as claimed in claim 1, said plurality of apertures being arranged in a predetermined pattern, said pattern including a circular series of said apertures.

3. A face plate assembly as claimed in claim 2, the angular spacing between apertures in said circular series being 20 degrees.

4. A face plate assembly as claimed in claim 3, said index plate having a central opening passing therethrough, said circular series of apertures being concentric with the axis of said opening.

5. A face plate assembly as claimed in claim 4, said pattern of apertures including a number of apertures disposed on a pitch circle intermediate said circular series and said opening.

6. In a gas service delivery system for providing a selected plurality of gas services via a corresponding plurality of gas service outlet stations and cooperable adaptors wherein each such gas service outlet station includes a gas delivery means that is cooperable for connection only to an adaptor corresponding to the gas service available at the respective gas service outlet station, said gas delivery means comprising:

an open-faced mounting box for receiving therein a gas service conduit connector, said box having an opening formed in the rear wall thereof to define a display window;

adaptor connection means cooperable with said mounting box for installation in the respective gas service outlet station and for connection thereof to such gas service conduit connector;

indexable indicia means selectively positionable in any of a plurality of positions with respect to said box to indicate through said display window of the said mounting box the identity of the selected gas service connected to such gas service conduit connector and to provide a keying scheme to permit installation in said mounting box of only a said adaptor connection means which is configured to be connected with adaptors corresponding to the gas service indicated in said gas service identity display;

said adaptor connection means corresponding to the selected gas service including keying means for cooperating with said indexable indicia means to allow mounting of said adaptor connection means in said box only when said indexable indicia means is positioned to indicate through said display window the selected gas service;

adaptor connection means mounting means for mounting said adaptor connection means in position in said box;

and said box including means cooperable with said indexable indicia means for maintaining the selected position thereof with respect to the box.

7. The gas delivery means as claimed in claim 6 wherein said indexable indicia means is rotationally indexable with respect to said box.

8. The gas delivery means as claimed in claim 7 wherein said indexable means includes means mechanically engagable with said box in a plurality of rotationally distinct positions corresponding to such selected plurality of gas services.

9. The gas delivery means as claimed in claim 7 wherein said indexable indicia means includes disc means adapted to be retained in any one of a plurality of rotationally distinct positions with respect to said box.

10. The gas delivery means as claimed in claim 9 wherein said disc means includes gas service label means located thereon to register with said display window of said box to provide a gas service identity display for the respective ones of said rotationally distinct positions corresponding to such selected plurality of gas services.

11. The gas delivery means as claimed in claim 6 wherein said mounting box additionally includes orientation keying means cooperable with said adaptor connection means to correctly orient the latter with respect to said mounting box.

* * * * *